United States Patent [19]
Suggitt

[11] 3,962,362
[45] June 8, 1976

[54] METHOD FOR PREPARING POLYPHENYLS
[75] Inventor: Robert M. Suggitt, Wappingers Falls, N.Y.
[73] Assignee: Texaco Development Corporation, New York, N.Y.
[22] Filed: Mar. 31, 1975
[21] Appl. No.: 563,754

[52] U.S. Cl............................ 260/668 R; 260/667; 260/668 D; 260/670
[51] Int. Cl.².......................................... C07C 15/12
[58] Field of Search............ 260/668 R, 667, 668 D

[56] References Cited
UNITED STATES PATENTS
3,784,618   1/1974   Suggitt et al.................... 260/668 R
3,784,619   1/1974   Crome et al................... 260/668 R

*Primary Examiner*—C. Davis
*Attorney, Agent, or Firm*—T. H. Whaley; C. G. Ries; Carl G. Seutter

[57] ABSTRACT

Polyphenyls including biphenyl and terphenyl, are prepared by hydroalkylation of a charge benzene, dehydrogenation of hydroalkylate, and separation of desired product polyphenyls.

13 Claims, 1 Drawing Figure

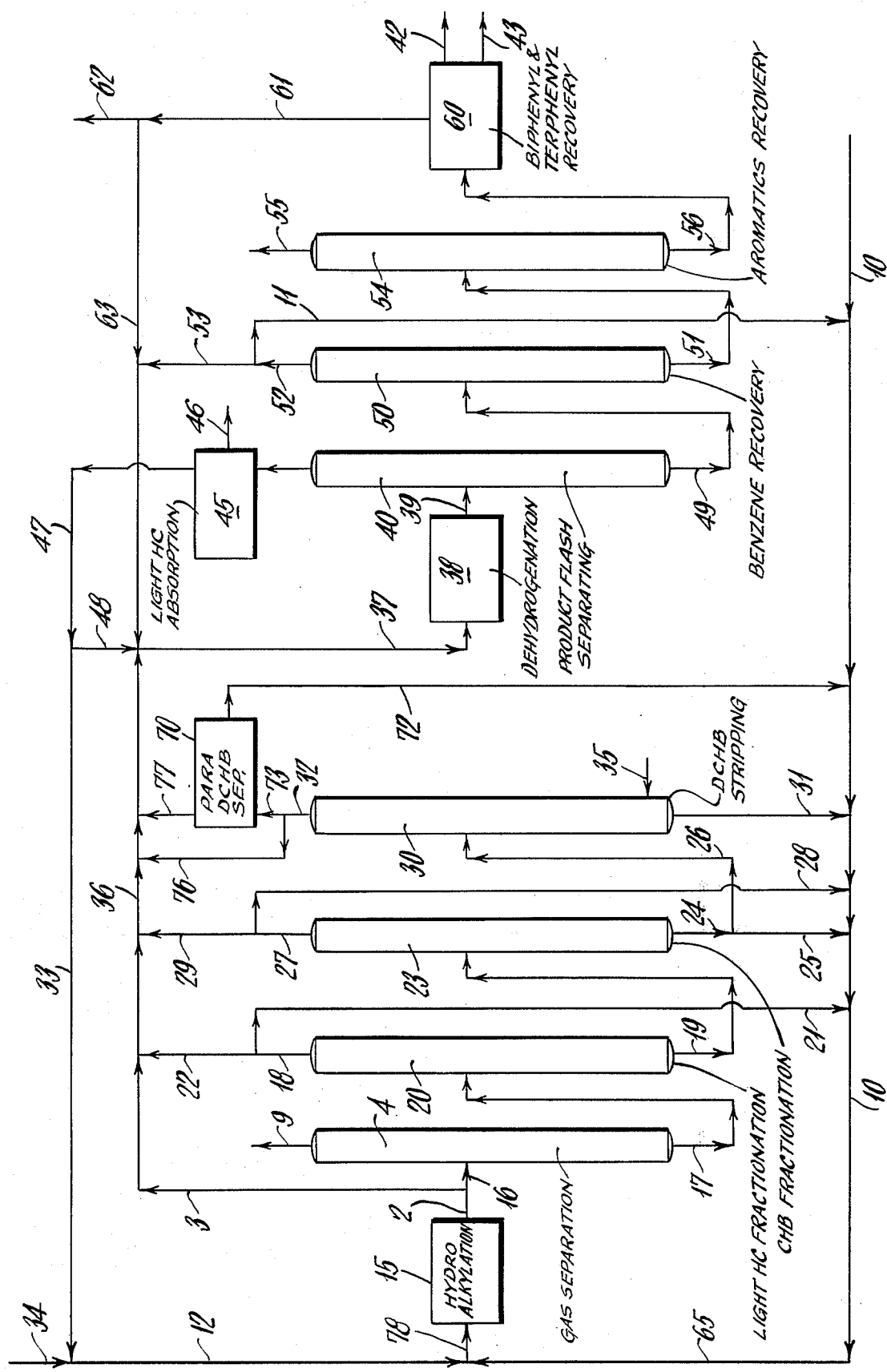

METHOD FOR PREPARING POLYPHENYLS

BACKGROUND OF THE INVENTION

This invention relates to the preparation of polyphenyls by hydroalkylation followed by selective dehydrogenation of cyclohexyl benzenes. More particularly this invention relates to the dehydrogenation of products of hydroalkylation under controlled conditions to form desired aromatic hydrocarbons.

As is well known to those skilled in the art, higher molecular weight aromatics, typified by biphenyls and terphenyls may be difficult to prepare in high purity because of their high boiling point which precludes distillation at reasonable temperatures and pressures. Among the techniques used to recover such materials may be noted vacuum distillation, crystallization, etc. It may be difficult to attain these materials in high purity because many techniques by which they may be recovered, give undesirable yields of by-products or require very severe processing conditions.

It is an object of this invention to provide a process for preparing selected aromatic hydrocarbons. It is a further object of this invention to provide a process for hydroalkylating a benzene to a cyclohexyl benzene followed by dehydrogenating the cyclohexyl benzene to form aromatic components and to permit recovery of these aromatic components. Other objects will be apparent to those skilled in the art.

SUMMARY OF THE INVENTION

In accordance with certain of its aspects, the novel process of this invention may comprise hydroalkylating a charge monocyclic aromatic hydrocarbon stream with a hydroalkylating quantity of hydrogen in the presence of hydroalkylation catalyst at hydroalkylation conditions thereby forming a hydroalkylate product stream containing naphthenyl benzenes;

dehydrogenating, in the presence of dehydrogenating catalyst at dehydrogenation conditions, a dehydrogenation charge stream containing at least a portion of the naphthenyl benzenes in said hydroalkylate product and at least one diluent-carrier selected from the group consisting of benzene, cyclohexyl benzene, methylcyclopentane, cyclohexane, toluene, xylene, and mixtures thereof thereby forming a dehydrogenated product stream containing polyphenyls in diluent-carrier, said diluent-carrier being of lower molecular weight than said product polyphenyls; and recovering said polyphenyls from said dehydrogenated product stream.

DESCRIPTION OF THE INVENTION

The charge mononuclear aromatic hydrocarbons which may be hydroalkylated by the process of this invention may include benzenes, including substituted benzenes, such as benzene se, toluene, xylenes, etc. The preferred charge may be benzene se.

Hydroalkylation may preferably be effected in one embodiment by passing to the hydroalkylation operation a charge mononuclear aromatic hydrocarbon, typically benzene, together with recycled materials, typically dicyclohexylbenzenes. Among the latter may be ortho-dicyclohexylbenzene, meta-dicyclohexylbenzene, and para-dicyclohexylbenzene.

The typical charge which may be hydroalkylated by the process of this invention may include, in addition to fresh charge benzene, other components including cyclohexylbenzene, para-dicyclohexylbenzene, tricyclohexylbenzenes, etc. The composition of the total charge (ex hydrogen) entering the reactor may include:

| Components | Parts | Typical |
|---|---|---|
| B | 40–90.5 | 92.6 |
| CHB | 0–5 | 0.6 |
| om-DCHB | 0.5–15 | 5.2 |
| p-DCHB | 0–15 | 1.5 |
| MCP | 0–10 | 0 |
| CH | 0–15 | 0 |

In this table, as in certain other tables in this description, for convenience, the following abbreviations indicate the noted compositions:

| Abbreviation | Composition |
|---|---|
| MCP | Methylcyclopentane |
| CH | Cyclohexane |
| B | Benzene |
| CHB | Monocyclohexyl benzene |
| CHB Impurities | Impurities, such as methylcyclopentyl benzenes, which boil within the boiling range of the CHB fraction |
| DCHB | Dicyclohexyl benzenes |
| DCHB Impurities | Impurities which boil within the boiling range of the DCHB fraction |
| om-DCHB | A mixture of ortho-DCHB and meta-DCHB |
| p-DCHB | Para-DCHB |
| DCH | Dicyclohexyl |
| TCHB | Tricyclohexyl benzenes |
| BP | Biphenyls |
| TP | Triphenyls |

Other components may be present, including methyl cyclopentyl benzenes, tricyclohexyl, tricyclohexyl benzenes, etc.

Preferably 100 parts by weight of benzene and a hydroalkylating quantity, preferably 0.2–10 parts, more preferably 0.2–3 parts, say 1.1 parts by weight of hydrogen may be employed for hydroalkylation.

Hydroalkylation may be effected in the presence of a hydroalkylation catalyst and a hydroalkylating quantity of hydrogen. The hydrogen need not be pure; but preferably hydrogen of 80%–100% purity may be used. The hydrogen should preferably be free of any impurities which may poison the catalyst. Hydrogen recovered from a reforming operation may be suitable.

The catalyst may contain a Group VIII transition metal component, e.g., cobalt, nickel, ruthenium, rhodium, palladium, iridium, and platinum. The preferred type of catalyst may include a Group VIII metal, typically nickel or cobalt, and it may also contain 0–30%, typically 10%–20%, say 19% of a Group VI metal, typically tungsten, on a silica-alumina catalyst support. When the Group VIII metal is Co or Ni, it will preferably be present in an amount of 2%–30%, typically 4%–25%, say 22%. When the Group VIII metal is a noble metal, it may be present in amount of 0.2%–5%, say 1%. Such a catalyst may be prepared for example by impregnating or ion-exchanging a commercial $NH_4$-exchanged Y zeolite catalyst with e.g. nickel nitrate (or cobalt nitrate) and thereafter with ammonium meta-tungstate solution and then drying the catalyst in air at say 100°C. The so-dried catalyst may be further dried at 150°C. and then calcined to a maximum temperature up to 800°C.

The catalyst may be calcined during which residual nitrates are decomposed and the catalyst is dehydrated.

The catalyst may (preferably after loading into the hydroalkylation unit) be reduced in the presence of hydrogen for a minimum of 1 hour and typically at least 4–8 hours at a temperature preferably above about 300°C. and typically 300°–700°C, say 500°C.

The so-prepared typical catalyst may contain, on a dry basis, 6% nickel, 19% tungsten, and 22% hydrogen-Y zeolite, the remainder being amorphous silica-alumina support.

Hydroalkylation of aromatic feed may be effected by using this catalyst at an LHSV of 1.0–15, typically 2–10, say 3.

The pressure of hydroalkylation may typically be 100–1500 psig preferably 100–500 psig, say 500 psig; at this pressure the reactants are maintained substantially in liquid phase — except for the hydrogen which is in gas phase.

Hydroalkylation may be carried out in one reactor or more preferably in at least two reactors in series. The partially hydroalkylated effluent from the first hydroalkylation operation may be passed to a subsequent hydroalkylation operation wherein additional hydrogen is admitted and further hydroalkylation may occur.

The amount of hydrogen admitted to the first reactor may typically be greater than the amount calculated from the total amount of hydrogen added in all the hydroalkylation operations divided by the number of hydroalkylation operations.

In a preferred embodiment, hydroalkylation may be carried out by passing the charge hydrocarbon and a first portion of the hydroalkylating quantity of hydrogen through a first hydroalkylation operation at hydroalkylation conditions. In one preferred embodiment, hydroalkylation may be effected in two operations; and the amounts of hydrogen admitted to each of the hydroalkylation operations may be substantially equal.

Typically, however, when two stages are employed, the hydrogen admitted to the first hydroalkylation operation may be greater than about 50%, e.g. 50%–70%, say 55%, of the hydroalkylating quantity of hydrogen; and that admitted to the second hydroalkylation operation may be less than about 50%, e.g. 30%–50%, say 45%.

If hydroalkylation be carried out in three steps, the quantity of hydrogen admitted to the first zone may be 35%–45%, say 40% of the total hydrogen admitted; the quantity admitted to the second zone may be 30%–35%, say 35% of the total; and the quantity admitted to the third zone may be 20%–30%, say 25%.

Typically the inlet temperature to the first operation may be lower than the inlet temperature to subsequent operations; and consequently more hydrogen may be permitted to react in the first zone or operation without exceeding a preferred upper limit of temperature. Generally the fresh charge benzene is more reactive than is the mixed hydroalkylation product; and thus a lower inlet temperature may be used in the first hydroalkylation operation.

It is a feature of the process of this invention that each of the hydroalkylation operations be carried out at maximum operating temperature of less than about 250°C. (482°F.) and preferably at less than 210°C. (410°F). typically, temperature may be 100°–210°C, say 190°C, (375°F) and the hydrogen partial pressure may be 50–1500 psig, preferably 100–1500, more preferably 100–700 psig, say 500 psig.

The temperature of reaction may in one embodiment be controlled by cooling the feed to each hydroalkylation operation to a temperature of 20°–150°C, preferably 40°–100°C, say 80°C below maximum operating temperature. Thus the feed to a hydroalkylation operation may be at 80°–200°C, preferably 100°–190°C, say 125°C. As hydroalkylation occurs in one hydroalkylation operation, the temperature rises within the operating temperature range.

As will be apparent, the composition of the hydroalkylate product will be a function of the charge to the hydroalkylating operation. In one typical embodiment, wherein the charge benzene is benzene se plus recycle ortho-dicyclohexylbenzene, meta-dicyclohexylbenzene, and para-dicyclohexylbenzene, the product may typically contain the following:

TABLE

| Component | Preferred parts |
|---|---|
| B | 58.9 |
| CHB | 28.0 |
| OM-DCHB | 5.4 |
| p-DCHB | 2.6 |
| MCP | 0.8 |
| CH | 3.8 |
| DCH and others | 0.9 |

In the preferred embodiment, the hydroalkylate product in amount of 100 parts may be passed, in liquid phase, to a separation operation wherein any hydrogen present may be flashed off.

The product (100 parts) contains preferably 44 parts of unconverted benzene, 21.6 parts of cyclohexyl benzene, 10.9 parts of dicyclohexyl benzenes, and 0.9 parts of tricyclohexyl benzenes. Lesser quantities of other components may be present in the hydroalkylate to be further treated by the process of this invention.

The naphthenyl benzene hydrocarbon products of hydroalkylation which may be treated by the process of this invention may be characterized by the presence of an aromatic ring and at least one naphthenyl cyclohexyl ring. Typically this cyclohexyl benzene charge hydrocarbon may be represented by the formula:

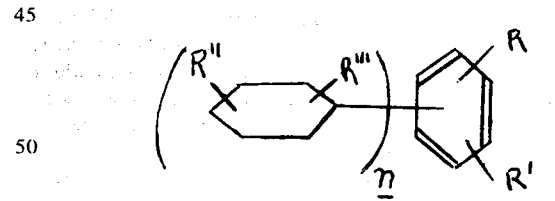

In the above formula $n$ may be an integer 1–4 preferably 1 or 2. R, R', R'', and R''' may be hydrogen or lower alkyl; when R, R', R'', or R''' is lower alkyl, it may preferably be methyl or ethyl.

In a preferred embodiment, the naphthenyl cyclohexyl group and the aromatic benzene ring may contain the same number of carbon atoms and may possess the same configuration. For example, if the naphthenyl moiety is cyclohexyl se, the aromatic moiety may be phenyl; if the naphthenyl moiety is methylcyclohexyl, the aromatic moiety may be tolyl; etc. The naphthenyl moieties may be different if benzene and xylene are simultaneously charged.

Typical examples include where $n = 1$ cyclohexylbenzene, methylcyclohexyl toluenes (12 isomers), (ethylcyclohexyl) ethyl benzenes, (dimethylcyclohexyl) xylenes, etc;

```
              Where n = 2
              para-dicyclohexylbenzene
              meta-dicyclohexylbenzene
              ortho-dicyclohexylbenzene
              dicyclohexyl toluenes
              di(ethylcyclohexyl) ethylbenzenes
              (methylcyclohexyl) cyclohexylbenzenes
              di (methylcyclohexyl) toluenes
              di (dimethylcyclohexyl) xylenes
        n = 3   1,3,5 tricyclohexylbenzene
              1,2,4,tricyclohexylbenzene
              tri(methylcyclohexyl) toluenes
              tri(ethylcyclohexyl) ethylbenzenes
```

Mixtures of (substituted cyclohexyl) substituted benzenes can be formed by hydroalkylating substituted benzene. For example the hydroalkylation of benzene results in a mixture that contains (aside from unreacted benzene) cyclohexylbenzene, dicyclohexylbenzenes (para, meta, and ortho isomers) and tricyclohexylbenzenes.

The hydroalkylation of toluene forms a mixture containing (methylcyclohexyl) toluenes, di(methylcyclohexyl) toluenes, and tri(methylcyclohexyl) toluenes.

In hydroalkylating xylenes, (dimethylcyclohexyl) xylenes and di(dimethylcyclohexyl) xylenes and tri (dimethylcyclohexyl) xylenes are formed.

When mixtures of aromatics, such as benzene and toluene or $C_6-C_8$ aromatics are hydroalkylated, additional compounds may be formed such as:

cyclohexyl toluenes
(methylcyclohexyl) benzenes
methylcyclohexyl cyclohexyl toluenes
methylcyclohexyl cyclohexyl benzenes
di(methyl cyclohexyl) benzenes
dicyclohexyl toluenes
cyclohexyl xylenes
cyclohexyl ethylbenzenes
methylcyclohexyl xylenes
(ethyl cyclohexyl) xylenes
di(ethylcyclohexyl) xylenes
(ethylcyclohexyl) (dimethylcyclohexyl) ethylbenzene
(ethylcyclohexyl) (dimethylcyclohexyl) xylenes
(ethylcyclohexyl) cyclohexyl toluenes
(ethylcyclohexyl) cyclohexyl benzenes
(ethylcyclohexyl) cyclohexyl xylenes While a large number of isomers of (substituted cyclohexyl) substituted benzenes can be formed by hydroalkylation many of these isomers occur, if at all, in very low concentrations. In particular the formation of isomers where an alkyl group is substituted on the same carbon that bonds the cyclohexyl group to the benzene ring are sterically not favored during hydroalkylation. For example, when hydroalkylating toluene, the formation of the following isomers is not favored because of steric factors:

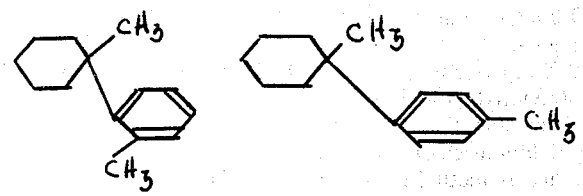

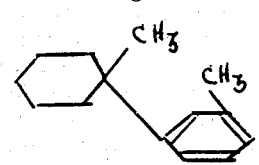

It is a feature of the process of this invention that such compounds as these are not preferred materials.

Similarly it is understood that when the (dimethylcyclohexyl) benzenes, (dimethylcyclohexyl) toluenes, and (dimethylcyclohexyl) xylenes are formed by hydroalkylating an aromatic containing xylenes, the two methyl groups on the cyclohexyl ring are not attached to the same carbon. That is, the carbon in the cyclohexyl ring to which a methyl group is attached must also have a hydrogen substituent to permit the facile dehydrogenation of the cyclohexyl ring.

It is a feature of the process of this invention that the hydroalkylating reaction does not favor the formation of such undesirable compounds as described above. Thus the hydroalkylating reaction is ideally suited for the preparation of the feed materials for the following steps of the process of this invention.

It is to be appreciated that other compounds can be formed in minor amounts during the hydroalkylation. Some, such as dicyclohexyl or other substituted bicyclohexyls, are suitable feed material for the subject process. However, most byproducts of the reaction do not contribute substantially to the desired products.

For example, during the hydroalkylation of benzene, (methylcyclopentyl) benzenes are formed which possess physical properties similar to cyclohexylbenzene and hence are difficult to separate from the cyclohexylbenzene. Likewise, the dicyclohexylbenzene distillate fraction contains impurities such as (methylcyclopentyl) cyclohexylbenzenes. While the dicyclohexylbenzenes are preferred materials for forming terphenyls, the impurities do not generate terphenyls, although some biphenyls can be formed if the methylcyclopentyl group can be cracked off.

In addition, when hydroalkylating benzene, cyclohexane and methylcyclopentane are also formed.

Similar cyclopentyl impurities are formed in hydroalkylating toluene, xylenes, and ethyl benzenes or mixtures thereof with or without benzene.

In addition, naphthenes corresponding to the feed aromatic are also formed during hydroalkylation. Thus, for example, cyclohexane and methylcyclopentane are formed during the hydroalkylation of benzene. Likewise methylcyclohexane and dimethylcyclopentanes are generated during the hydroalkylation of toluene; dimethylcyclohexanes and trimethylcyclopentanes in hydroalkylation of xylenes; and ethylcyclohexane and methylethylcyclopentanes in hydroalkylation of ethylbenzene.

These saturated naphthenes are inert under hydroalkylation conditions. That is, cyclohexane does not react with benzene to make cyclohexylbenzene. It has been heretofore necessary then to eventually separate these naphthenes from the charge aromatic and then dispose of them.

It is a feature of the process of this invention that these saturated naphthenes may be included in the (substituted cyclohexyl) substituted benzene feed either for dehydrogenation back to the parent aromatic as in the case of the cyclohexane derivatives or for cracking to light product as in the case of the cyclopentane derivatives. In either event, their inclusion in the feed to the process of the invention together with nonhydroalkylated aromatic, e.g. benzene, toluene, xylenes, or ethylbenzene, can provide a means of reconcentrating or purifying the feed aromatic prior to recycling the aromatic back to the hydroalkylation reactor.

Although the entire hydroalkylate product (including hydrogen, unconverted benzene, and "by-products" as well as desired cyclohexylbenzene product) may be passed directly to a dehydrogenation operation, it is preferred that at least a portion of the hydrogen present be separated in a gas separation operation. Liquid bottoms from this gas separation operation, preferably substantially free of hydrogen, typically contain benzene, cyclohexylbenzene, cyclohexane, and dicyclohexyl benzene together with lesser quantities of methyl cyclopentane, tricyclohexyl benzene, cyclohexyl benzene impurities, and dicyclohexyl benzene impurities.

This bottoms stream is passed to a light hydrocarbon fractionation operation. Overhead therefrom typically contains benzene and cyclohexane together with lesser quantities of methyl cyclopentane. At least a portion and preferably a major portion, of this overhead is passed to dehydrogenation. Optionally a portion of the overhead from light hydrocarbon fractionation may be recycled to hydroalkylation.

The bottoms from light hydrocarbon fractionation contains principally cyclohexyl benzene and dicyclohexyl benzenes together with lesser quantities of tricyclohexyl benzenes, cyclohexyl benzene impurities, and dicyclohexyl benzene impurities. This stream is passed to a cyclohexyl benzene fractionation operation from which an overhead stream is recovered containing principally cyclohexyl benzene together with a small quantity of cyclohexyl benzene impurities.

If it is the overall objective of the process to produce increased yields of diphenyls, then the cyclohexyl benzene-containing overhead stream is passed directly to dehydrogenation. If, on the other hand, the overall objective of the process is to produce increased yields of terphenyls at the expense of diphenyls, then the cyclohexyl benzene fraction is recycled to hydroalkylation where it is converted to dicyclohexyl benzenes and suppresses the formation of additional cyclohexyl benzenes.

The bottoms steam from cyclohexyl benzene fractionation contains principally dicyclohexyl benzenes together with lesser quantities of dicylclohexyl benzene impurities and tricyclohexyl benzenes. If the overall process requirements are such that biphenyls are the desired product, then this bottom stream is passed to hydroalkylation wherein the dicyclohexyl benzenes are converted to cyclohexyl benzene and the formation of additional dicyclohexyl benzenes and tricyclohexyl benzenes is suppressed.

In a preferred embodiment, bottoms from the cyclohexyl benzene fractionation operation are passed to a dicyclohexyl benzene stripping operation wherein they are preferably subjected to stripping with hydrogen as the stripping gas. Bottoms recovered contain principally dicyclohexyl benzenes together with lesser quantities of tricylcohexyl benzenes and dicylcohexyl benzene impurities. This stream may be discarded or more preferably recycled to hydroalkylation.

The overhead stream from the dicyclohexyl benzene stripping operation, when separated from hydrogen stripping gas, contains principally dicyclohexyl benzenes and a lesser quantity of dicyclohexyl benzene impurities. This stream may be passed directly to dehydrogenation or it may be passed to a paradicyclohexyl benzene separation unit. Separation of paradicyclohexyl benzene is carried out preferably by the process disclosed in U.S. Pat. No. 3,784,619 which issued Jan. 8, 1974 to Texaco Inc. as assignee of John M. Crone Jr. and Robert M. Suggitt. The paradicyclohexyl benzene so recovered is preferably passed to dehydrogenation.

The reject stream from paradicyclohexylbenzene separation, which contains mainly metadicyclohexyl benzene toeether with some orthodicyclohexyl benzene, may be recycled to hydroalkylation.

In another embodiment, the overhead stream from dicyclohexyl benzene stripping may by-pass the paradicyclohexyl benzene separation operation and be passed directly to dehydrogenation.

Charge to dehydrogenation may thus include (i) monocyclohexyl or polycyclohexyl benzenes preferably dicyclohexyl benzenes and tricyclohexyl benzenes, (ii) hydrogen, and (iii) at least one diluent-carrier liquid preferably selected from the group consisting of methylcyclopentane, cyclohexane, toluene, xylene, benzene, cyclohexyl benzene, and mixtures thereof.

It will be apparent to those skilled in the art that if the ultimate product desired is pure biphenyl, then the charge to dehydrogenation will contain substantial quantities of cyclohexyl benzene and be free of polycyclohexyl benzenes. Similarly if the desired ultimate product is high purity terphenyls, then the charge to dehydrogenation will contain dicyclohexyl benzenes to the substantial exclusion of monocyclohexyl benzene. Commonly however when the product is to be used as a functional fluid, it may be satisfactory or even desirable to have it contain both biphenyls and terphenyls; and in this instance the charge to dehydrogenation will preferably contain both monocyclohexyl benzene and dicyclohexyl benzenes.

The particular composition of the feed to dehydrogenation will be dictated by the products desired. For example, if para-terphenyl is desired, then the feed should contain para-dicyclohexylbenzene such as may be provided either as a mixture or with futher purification (e.g. as by the processes disclosed in U.S. Pat. Nos. 3,784,617 or 3,784,618 or 3,784,619). Likewise to make meta-terphenyl, the feed should contain metadicyclohexylbenzene.

It is a feature of the process of this invention, in accordance with certain of its aspects that dehydrogenation be carried out in the presence of a diluent-carrier which is preferably in liquid phase during dehydrogenation and steps immediately following. The diluent-carrier is characterized by the following properties:

a. it is desirably in liquid phase (at least in part) during dehydrogenation;

b. it preferably forms with the heavier products, including biphenyl and terphenyl, a fluid, flowing liquid or slurry whereby the reaction mixture passes readily through the dehydrogenation operation;

c. it is of lower molecular weight and of lower melting and boiling point than the desired product biphenyl or terphenyl.

It will be apparent that when the desired polyphenyls are biphenyls, the charge to dehydrogenation may include principally cyclohexyl benzene, hydrogen and, as liquid diluent-carrier, principally either benzene, cyclohexane, or methyl cyclopentane or a mixture thereof.

When the desired polyphenyls are terphenyls, the charge may include principally dicyclohexyl benzenes, hydrogen, and, as diluent-carrier, principally either benzenes, cyclohexane, cyclohexyl benzene, or methyl cyclopentane, or mixtures thereof. When the desired principal product is a mixture of biphenyls and terphenyls, the charge to dehydrogenation may include cyclohexyl benzene, dicyclohexyl benzenes, hydrogen, and as diluent-carrier principally either benzene, cyclohexane, methylcyclopentane or mixtures thereof.

It is a feature of the diluent-carrier liquid that it is inert during the conditions of dehydrogenation. It may be inert in the sense that it passes through dehydrogenation totally unchanged as may be the case with benzene. It may be inert in the sense that during dehydrogenation it is converted to a composition which is desirable as is the case with cyclohexane which may be converted to benzene — or it is converted to a product which is neutral i.e. it neither helps nor hinders the desired operation.

It may be inert in a particular operation (eg if the desired product were terphenyl) as would be the case for cyclohexyl benzene which in this instance, might be converted to biphenyl by-product.

Although it may be possible to use as diluent-carrier for the dehydrogenation operation, any composition which meets the above requisites, it is preferred that the diluent-carrier includes at least one composition selected from the group consisting of methyl cyclopentane, cyclohexane, benzene, toluene, xylene, cyclohexyl benzene, and mixtures thereof. Thus the diluent-carrier may typically be:

1. benzene
2. benzene cyclohexyl benzene
3. cyclohexyl benzene
4. methyl cyclopentane
5. cyclohexane
6. benzene cyclohexane
7. benzene cyclohexane cyclohexyl benzene
8. toluene
9. etc.

It may be desirable to use, as the diluent-carrier a $C_7$–$C_8$ aromatic eg toluene or xylene(s) — or other composition not present in or derived from the hydroalkylate; clearly however those found within the hydroalkylate (typically benzene, cyclohexane, methylcyclopentane, etc.) are the preferred liquid diluent-carriers.

In a preferred embodiment, the diluent-carrier may contain benzene, cyclohexyl benzene, and cyclohexane. In a more preferred embodiment, the charge to dehydrogenation may include substantially the total hydroalkylate; and in this instance the diluent-carrier may be considered to be the entire stream except for the dicyclohexyl benzenes and tricyclohexyl benzenes i.e. those components of hydroalkylate (ex hydrogen) which have a lower molecular weight than does dicyclohexyl benzene.

When the hydroalkylate is passed directly to dehydrogenation, it will be apparent that the lighter components including principally the benzene, methylcyclopentane, and cyclohexane may serve as the diluent carrier. At least about 0–80 wt %, typically 0–50 wt %, say abut 30 wt % of the benzene, methylcyclopentane, and cyclohexane contained in the hydroalkylate may be passed to dehydrogenation.

Typically the charge stream to dehydrogenation may contain an amount of benzene and cyclohexane equivalent to (i.e. present in equimolar amounts with) the heavier i.e. the dicyclohexyl benzenes plus tricyclohexyl benzenes. Alternatively expressed the mole ratio of benzene plus cyclohexane to dicyclohexyl benzene plus tricyclohexyl benzene in the charge to dehydrogenation may be 1–30:1, preferably 3–15:1, say 3:1.

Clearly diluent-carrier may be recovered and passed to dehydrogenation from various sources including recovery from the product dehydrogenated stream.

In practice of the process of this invention according to certain of its aspects, dehydrogenation may be effected in a non-oxidative atmosphere at dehydrogenation condition in the process of non-acidic dehydrogenating catalyst preferably containing at least one metal selected from the group consisting of rhenium, Group VI B metals, and Group VIII metals thereby forming a dehydrogenated stream containing (i) desired aromatic components and (ii) undesired components having a cyclohexyl-aromatic bond.

The non-oxidative atmosphere in which the process of this invention may be carried out may be the autogenous atmosphere generated during the reaction. In another embodiment, the atmosphere may contain 0–50, typically 1–20, say 3 moles (per mole of charge) of hydrogen admitted with the hydrocarbon charge. Inert diluents such as nitrogen, steam, etc. may be present in amount of 0–100 moles, typically 1–20 moles, say 2 moles per mole of hydrocarbon charge.

In one preferred embodiment, there may be admitted with the charge at least a portion of the recycled product stream either before or after the latter is purified.

Dehydrogenation is carried out at dehydrogenation conditions including a temperature of 700°–1100°F., preferably 750°–950°F., say 885°F. and at a total pressure of 0–100 psig, preferably 50–100 psig, say 50 psig at LHSV of 0.1–10, say 2.

Reaction may be carried out in the presence of a non-acidic catalyst. Catalyst supports which may be employed as non-acidic supports include neutral and basic supports. Typically such supports contain basic moieties in their structure (including groups adsorbed thereon) or they may be neutral. In preferred embodiments, they may be pretreated with aqueous caustic (e.g. sodium hydroxide or more preferably potassium hydroxide) and calcined. Typical of such supports are base-leached carbon, caustic washed alumina, potassium hydroxide-treated alumina, silica gel, etc. A typical alumina may contain 0.5% $Li_2O$ or 1.5% $K_2O$.

A non-acidic alumina can be distinguished from an acidic alumina by contacting a sample of the freshly calcined alumina (5 hours at 500°C.) with a solution of dry benzene saturated with phenolphthalein. When so contacted, non-acidic aluminas remain colorless, while acidic aluminas form a red color of a shade distinctly different from the well known purple color of phenolphthalein in basic media. Adding water to the red colored dry alumina impregnated with phenolphthalein causes a slow fading of color in the case of truly acidic alumina. When water is added to colorless samples of basic aluminas (those containing sizeable amounts of alkali) impregnated with with phenolphthalein, an intense purplish red color develops in the water layer.

There may be deposited on and within the support at least one metal selected from the group consisting of rhenium Re, a Group VI B metal, and a Group VIII metal. When the metal is a Group VI B metal, it may be chromium Cr, molybdenum Mo, or tungsten W. When the metal is a Group VIII metal it may be iron Fe, cobalt Co, or mickel Ni or more preferably a noble metal including ruthenium Ru, rhodium Rh, palladium Pd, iridium Ir, or platinum Pt. The preferred metal may be a metal of Group VIII, preferably platinum, or a combination of Group VIII platinum metals such as Pt-Ir.

When more than one metal is present, it may be e.g. nickel-chromium but more preferably it is preferred that it be a Group VIII noble metal plus a Group VI B metal; e.g. platinum-molybdenum, platinum-rhenium, etc. When the metal is nickel or cobalt, it is particularly preferred that a Group VI B metal be present.

The catalyst may contain the metal (when the metal is cobalt or nickel) in amount of 2–15 parts, preferably 3–10 parts, say 5 parts per 100 parts of support. When the metal is a Group VI B metal it may be present in amount of 5–40 parts, preferably 10–30 parts, say 20 parts (e.g. of $Cr_2O_3$ or $Mo_2O_3$ per 100 parts of support).

The catalyst may be typically prepared, in one embodiment, by contacting a low ash activated carbon in an impregnating solution containing potassium carbonate and ammonium chloroplatinate in sufficient amounts to provide 1.0% $K_2O$ and 0.8 percent platinum on drying. The catalyst may then be calcined in an non-oxidizing atmosphere, e.g. in nitrogen at 500°C.

Alternatively, in another typical embodiment, a catalyst may be prepared by impregnating an alumina with a solution containing potassium nitrate and ammonium molybdate in sufficient amounts to provide a composition on drying and calcining that contains by weight 1.5% $K_2O$ and 20% $Mo_2O_3$.

The catalyst may be activated by contact with flowing hydrogen at 700°–1100°F., preferably 750°–1000°F. say 875°F.

In accordance with practice of the process of this invention, dehydrogenation may be effected to convert the cyclohexyl aromatic to a desired aromatic component in which the product cyclohexyl-derived moiety contains less hydrogen than does the charge cyclohexyl moiety. In the preferred embodiment, the charge cyclohexyl moiety is selectively converted to high yields of aromatic moiety—and in typical operation, the charge cyclohexyl moiety may be selectively converted to aromatic moieties in conversion of 30%–100%, preferably 50%–100%, say 70%.

During dehydrogenation, the following typical reaction may occur in the case of the conversion of dicyclohexyl benzene to terphenyl:

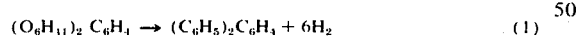

$$(C_6H_{11})_2 C_6H_4 \rightarrow (C_6H_5)_2 C_6H_4 + 6H_2 \quad (1)$$

It may be noted that during hydroalkylation of benzene to produce the typical charge stream to the process of this invention, four net moles of hydrogen are used to make dicyclohexylbenzene when it is assumed that the intermediate product cyclohexylbenzene is recycled to the hydroalkylation reactor or

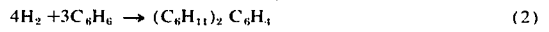

$$4H_2 + 3C_6H_6 \rightarrow (C_6H_{11})_2 C_6H_4 \quad (2)$$

It is then to be noted that, by combining the hydroalkylation reaction of benzene (2) with the dehydrogenation of the cyclohexylbenzene (1), in theory there is a net gain of hydrogen. Overall adding reaction (2) to reaction (1), the result is

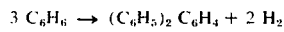

$$3 C_6H_6 \rightarrow (C_6H_5)_2 C_6H_4 + 2 H_2$$

In practice, side reactions consume hydrogen and a net gain of hydrogen is not experienced. However, it is to be noted that overall hydrogen consumption is mininal and no environmentally undesirable side products are generated.

Furthermore in generating biphenyl, overall yields can be high, hydrogen consumption mininal, by using relatively mild processing conditions.

The product stream may typically contain desired aromatic components containing less hydrogen than does the charge component and thus possessing a higher degree of unsaturation. In the preferred embodiment, the cyclic moieties in the product will contain a higher degree of aromatic unsaturation. In the case of dehydrogenation of e.g. cyclohexyl benzene, the product stream will contain the desired phenyl benzene (i.e. biphenyl). In the case of dehydrogenation of dicyclohexyl benzene, the product stream will contain the desired diphenyl benzene (i.e. terphenyl)—the latter compound is particularly useful as a heat transfer medium.

The product stream will also contain undesired naphthenyl aromatic components. In the case of dehydrogenation of cyclohexyl benzene, the product stream may contain undesired unconverted cyclohexyl benzene plus undesired benzene and methylcyclopentylbenzenes. In the case of charge dicyclohexyl benzene, the undesired components in the product stream may include cyclohexyl, phenyl benzene; dicyclohexenyl benzene; cyclohexyl, cyclohexenyl benzene; (methylcyclopentyl) phenylbenzene etc.

It is a feature of the process of this invention that unexpectedly the reaction conditions which are conducive to dehydrogenation of the cyclohexyl moiety in the charge cyclohexyl aromatic hydrocarbon desirably give little or no cracking of the cyclohexyl aromatic bond. Typically less than 30 wt.% of the charge is cracked by rupture of this bond.

When dehydrogenating a crude stream recovered for example from the hydroalkylation of benzene which may contain a mixture including benzene, cyclohexane, cyclohexylbenzene, methylcyclopentylbenzene, dicyclohexylbenzenes, (methylcyclopentyl) cyclohexyl benzene, etc., the dehydrogenation product mixture may contain:

benzene
methylcyclopentane
cyclohexane
biphenyl
methylcyclopentylbenzenes
methylcyclopentadieneylbenzenes
trace amounts of cyclohexylbenzene
terphenyls
cyclohexyl phenyl benzenes
(methylcyclopentyl), phenyl benzenes
dicyclohexylbenzenes When carried out in practice of the process of this invention, dehydrogenation of the charge liquid stream containing the preferred cyclohexyl benzene and dicyclohexyl benzenes permits ready formation of the high melting and high boiling biphenyl(m.p. 70°C., b.p. 254°C or 485°F.) and terphenyls. Although the temperatures during dehydrogenation are sufficiently high so that high melting materials including those noted are above their melting points, it may be found that it is not possible to maintain a single non-gas phase unless there be present a "dehydrogenated product-solubilizing amount" of liquid diluent-carrier, preferably benzene i.e. an amount of diluent-carrier sufficient to maintain fluidity in the dehydrogenation operation.

It is a feature of the process of this invention that the presence of the diluent-carrier insures that the flow through dehydrogenation is positive and continuous. The charge to dehydrogenation and the product stream therefrom are characterized by the presence of a liquid phase which is continuous; and the heavier components of the system (typically the desired products together with by-products) may be present in solution or slurry in the liquid phase — the latter containing a substantial portion of the diluent-carrier. Presence of diluent-carrier insures continuous flow of material through dehydrogenation.

Product leaving dehydrogenation typically includes (i) desired products including biphenyls and terphenyls, (ii) hydrogen, together with methane and light $C_2$ to $C_4$ hydrocarbons contained therein, (iii) diluent-carrier typically benzene, cyclohexane, methyl cyclohexyl benzene, $C_7$ to $C_8$ aromatics, or mixtures thereof and (iv) unconverted charge ingredients typified by cyclohexyl benzene, cyclohexyl benzene impurities, dicyclohexyl benzenes, dicyclohexyl benzene impurities, etc.

Recovery of desired products of dehydrogenation preferably includes flash separating to recover hydrogen together with any light hydrocarbons present. These latter are preferably recovered as by absorption; and the hydrogen is recycled to hydroalkylation or dehydrogenation or both.

Bottoms from product flash separation are typically passed to "benzene" recovery from which is recovered an overhead stream typically containing the diluent-carrier including for example benzene (the preferred diluent-carrier), cyclohexane, methyl cyclopentane, etc. At least a portion of this recovered stream is recycled to dehydrogenation depending upon the needs of the charge stream to dehydrogenation; and at least a portion is typically recycled to hydroalkylation.

Bottoms from "benzene" recovery are typically passed to an aromatics recovery operation. Overhead from this operation typically may include the $C_7$ and $C_8$ aromatics present in the bottoms from the "benzene" recovery operation. The bottoms recovered from the aromatics recovery operation typically contain 50 w %–80 w % biphenyls, 10 w %–20 w % terphenyls, and lesser quantities of cyclohexyl benzene and related naphthenyl benzenes, and dicyclohexyl benzenes and related dinaphthenyl benzenes.

Although it may be possible to use the so-recovered stream as a functional fluid (e.g., as a heat transfer medium) in this form, it may be desirable in certain embodiments to effect further fractionation to obtain a more pure bottoms containing biphenyl and terphenyls — overhead containing lower boiling components.

If it is desired to produce a product containing increased proportions of biphenyl or terphenyls, this may be effected by control of the charge to dehydrogenation. For use as functional fluids, it may be satisfactory to produce product containing predominantly biphenyl and terphenyls with lesser quantities of other components.

If it be desired to separate biphenyl and terphenyls to permit attainment of enriched products, this may be done as by vacuum distillation. In a more preferred embodiment, it may be desired to cool a mixture containing biphenyl and terphenyls to form a slurry of terphenyl crystals in liquor. After recovery of terphenyls as by filtration, the biphenyl may be subsequently recovered by further cooling and filtration. Low boiling solvents, such as toluene, may be present during cooling and filtration to facilitate handling.

EXAMPLE

Practice of the process of this invention may be apparent by reference to the drawing which schematically shows a process flow sheet according to which the process may be carried out. All parts referred to in this specification are parts by weight unless otherwise stated.

In practice of this embodiment of the process of this invention, charge includes 29.07 parts of fresh benzene admitted through line 10. In this particular embodiment, benzene is admitted through line 10 and is admixed with tricyclohexylbenzene bottoms from line 31 together with any recycle cyclohexylbenzene from line 28, any recycle dicyclohexylbenzene plus tricyclohexylbenzenes from line 25, and recycle methylcyclopentane, cyclohexane and benzene from line 21 to form charge hydrocarbon stream in line 65.

Recycle hydrogen in line 33, containing 2.21 parts hydrogen and 0.48 parts $C_1$–$C_2$ paraffins, is joined with 0.16 parts of fresh hydrogen in line 34 to form charge hydrogen stream in line 12.

The hydrogen in line 12 and the hydrocarbon mixture in line 65 are mixed and passed to hydroalkylation unit 15 through line 78. In this particular embodiment the charge hydrocarbon entering hydroalkylation operation through line 65 includes

| Component | Parts |
| --- | --- |
| MCP | 0.25 |
| CH | 0.82 |
| B | 94.77 |
| DCHB impurities | 0.08 |
| TCHB | 0.91 |
|  | 100 |

Charge to hydroalkylation operation 15 is passed into contact with hydroalkylation catalyst which includes 23 wt. % cobalt on rare earth-ammonium exchanged faujasite-type cracking catalyst (extruded to ⅓ inch diameter pellets, dried at 200°F, calcined to 1480°F over 4 hours, and reduced inflowing hydrogen at 900°F for 2 hours). Catalyst is arrayed in two beds.

100 parts of charge dry hydrocarbon and 1.30 parts of hydrogen (containing 0.26 parts methane) are admitted through line 78 to the first bed of hydroalkylation operation 15 at 250°F and 495 psig. The effluent from the first bed is cooled to 300°F and 495 psig and mixed with an additional 1.06 parts of hydrogen (containing 0.22 parts of methane); and the so cooled effluent is admitted to the second bed. (In the drawing, the beds are not shown separately, nor is the cooling operation between the beds shown). Effluent from hydroalkylation in line 2, recovered at temperature of less than 418°F, contains the following components:

| Component | Parts |
| --- | --- |
| Hydrogen | 0.05 |
| Methane | 0.48 |
| MCP | 1.08 |
| CH | 20.45 |
| B | 45.41 |
| CHB Impurities | 0.76 |
| CHB | 22.21 |
| DCHB Impurities | 0.28 |

-continued

| Component | Parts |
|---|---|
| DCHB | |
| om-DCHB | 5.79 |
| p-DCHB | 5.43 |
| Tricyclohexylbenzenes | 0.91 |
| Total | 102.85 |

It will be noted that only about 36 per cent of the feed hydrogen consumed is utilized to make the preferred cyclohexylbenzene and dicyclohexylbenzenes.

The remaining hydrogen is consumed in generating by-products such as cyclohexane, production of which consumers about 61 per cent of the feed hydrogen.

Recovery of by-products including cyclohexane (and in particular the hydrogen and benzene values contained therein) permits attainment of an economic process for preparation of biphenyl and terphenyls.

It is a feature of the process of this invention that a substantial portion of the hydrogen tied up in the cyclohexane may be recovered by including the benzene plus cyclohexane portion of the hydroalkylation effluent in the charge to the dehydrogenation operation. Benzene and cyclohexane also serve as a solvent and a carrier for the heavier compounds, e.g. the cyclohexylbenzene and dicyclohexylbenzenes. In addition, the benzene serves as a solvent and as a carrier for the dehydrogenation products-biphenyl and terphenyls. It is particularly important to have a solvent, such as a light aromatic, to fluidize the terphenyls as they possess extremely high melting points (for example m-terphenyl 365°C; p-terphenyl, subliming at 427°C), so that they may be swept from the dehydrogenation unit through lines 39 etc., to recovery units.

The entire effluent from hydroalkylation (including hydrogen and volatile components) in line 2 may be passed through lines 3, 36, and 37 to dehydrogenation unit 38 with no intermediate processing except adjustment of temperature and pressure. However, in one embodiment, all of the effluent in line 2 is passed through line 16 to gas separating operation 4. Overhead containing 0.05 parts hydrogen and 0.48 parts methane are withdrawn through line 9. Liquid containing:

| Component | Parts |
|---|---|
| MCP | 1.08 |
| CH | 20.45 |
| B | 45.41 |
| CHB Impurities | 0.76 |
| CHB | 22.21 |
| DCHB Impurities | 0.28 |
| DCHB | 11.22 |
| TCHB | 0.91 |
| Total | 102.32 | is drawn off through line 17 and routed to light hydrocarbon fractionator 20. Overhead from fractionator 20 containing:

| Component | Parts |
|---|---|
| MCP | 1.08 |
| CH | 20.45 |
| B | 45.41 |
| Total | 66.94 | is drawn off through line 18. A portion (less than 100 per cent) of the effluent in line 18 may be drawn off through line 21 and recycled back to hydroalkylation unit 15 through line 10 and 65. However, in this embodiment, all of the overhead in line 18 is routed through lines 22, 36, and 37 to dehydrogenation unit 38. This light hydrocarbon material acts as a solvent and fluidizer of the heavier fractions going to dehydrogenation in line 37 and the products from the dehydrogenation in line 39.

Bottoms from light hydrocarbon fractionator 20 are drawn off in line 19 and contain:

| Component | Parts |
|---|---|
| CHB Impurities | 0.76 |
| CHB | 22.21 |
| DCHB Impurities | 0.28 |
| DCHB | 11.22 |
| TCHB | 0.91 |
| Total | 35.38 |

The material in line 19 is routed to cyclohexylbenzene fractionator 23. Overhead, taken off through line 27, contains 0.76 parts cyclohexylbenzene impurities and 22.21 parts cyclohexylbenzene. 0% to 100% of this material may be routed back through lines 28, 10, and 65 to hydroalkylation depending upon the desired biphenyl-terphenyl product split. If, for example the production of biphenyl is to be minimized, then the cyclohexylbenzene fraction would be recycled back through line 28 to hydroalkylation unit 15 where it can be converted into dicyclohexylbenzenes, or suppress the formation of additional cyclohexylbenzene in hydroalkylation. If, however, as in this embodiment, biphenyl production is preferred, then all of the cyclohexylbenzene portion may be taken through line 29 to lines 36 and 37 to dehydrogenation unit 38. The bottoms from fractionator 23, are drawn off through line 24 and contain:

| Component | Parts |
|---|---|
| DCHB Impurities | 0.28 |
| DCHB | 11.22 |
| TCHB | 0.91 |

The disposal of cyclohexylbenzene fractionator bottoms in line 24 is dependent upon the desired product slate. If no terphenyls are desired, then all of these bottoms in line 24 are routed through lines 25, 10, and 65 to hydroalkylation 15 where they are either transalkylated with benzene to form additional cyclohexylbenzene or at least suppress formation of additional di- and tricyclohexylbenzenes. In this particular embodiment all of the cyclohexylbenzene fractionator bottoms in line 24 is routed through line 26 to dicyclohexylbenzene stripper unit 30. Hydrogen stripping gas can be added through line 35 to promote the vaporization of the dicyclohexylbenzenes. Hydrogen recovery from line 32 is not shown.

Hydrocarbon overhead from DCHB stripper unit 30, taken off through line 32, contains:

| | |
|---|---|
| DCHB Impurities | 0.20 |
| DCHB | |
| om-DCHB | 4.15 |
| p-DCHB | 3.90 |
| Bottoms comprising: | |
| DCHB Impurities | 0.08 |

| | |
|---|---|
| DCHB | 3.17 |
| TCHB | 0.91 | are drawn off through line 31 and may be discarded or as in this embodiment, recycled back through lines 10 and 65 to hydroalkylation unit 15.

The DCHB overhead in line 32 may be routed through lines 76, 36, and 37 to dehydrogenation unit 38 or it may optionally pass through line 73 to a paradicyclohexylbenzene separation unit 70 (q.v. U.S. Pat. No. 3,784,619) in order to permit preferential production of the paraterphenyl in dehydrogenation unit 38. Reject stream, comprising mainly meta dicyclohexylbenzene, is recycled through lines 72, 10, and 65 to hydroalkylation unit 15 where it is converted to desired products, e.g., cyclohexylbenzene, p-dicyclohexylbenzene or wherein it at least suppresses formation of additional m-dicyclohexylbenzene. In this particular embodiment all of the overhead in line 32 is routed through line 76 to 36 where it is combined with solvent methylcyclopentane, cyclohexane, and benzene from line 22 and cyclohexylbenzene in line 29 to form in line 36 a mixture of:

| Component | Parts |
|---|---|
| MCP | 1.08 |
| CH | 20.45 |
| B | 45.41 |
| CHB Impurities | 0.76 |
| CHB | 22.21 |
| DCHB Impurities | 0.20 |
| DCHB | 8.05 |

Material in line 36 is joined with recycle benzene in line 63 in amount sufficient to insure that a minimum weight ratio of 1 (preferably 3) parts of benzene plus cyclohexane to one unit of heavier component is present in line 37. Hydrogen is admitted through line 48.

In this particular embodiment, benzene recycle line 63 contains:

| Components | Parts |
|---|---|
| MCP | 0.17 |
| CH | 0.55 |
| B | 44.80 |

Hydrogen recycle line 48 contains:

| | Parts |
|---|---|
| Hydrogen | 4.95 |
| Methane | 1.05 |

The composition of the charge to dehydrogenation in line 37 is:

| | |
|---|---|
| Hydrogen | 4.95 |
| Methane | 1.05 |
| MCP | 1.25 |
| CH | 21.00 |
| B | 90.21 |
| CHB Impurities | 0.76 |
| CHB | 22.21 |
| DCHB Impurities | 0.20 |
| DCHB | 8.05 |
| Total | 149.68 |

It is seen that the 120.21 parts of benzene plus cyclohexane is in excess of three times the quantity of heavy material, namely 31.22 parts of the mononaphthenyl and dinaphthenylbenzenes.

The mixture in line 37 is passed to dehydrogenation operation 38 at 885°F, 50 psig, (2LHSV); dehydrogenation catalyst includes 0.75 wt % platinum on non-acidic gamma alumma which contains 1.2% $K_2O$.

Product leaving dehydrogenating operation 38 in line 39 includes

| Component | Parts |
|---|---|
| Hydrogen | 7.16 |
| Methane | 1.53 |
| Light hydrocarbon $C_2$–$C_4$ | 2.58 |
| MCP | 0.42 |
| CH | 1.37 |
| B | 110.50 |
| $C_7$–$C_8$ aromatics | 1.51 |
| biphenyl | 17.40 |
| terphenyls | 4.53 |
| CHB and similar mononaphthenyl benzenes | 2.32 |
| DCHB and similar dinaphthenylbenzenes | 0.36 |
| total | 149.68 |

It is also seen that the quantity of 111.87 parts of benzene plus cyclohexane is in excess of three (weight) times the 21.93 units of biphenyl and terphenyl and thereby serves as an effective solvent or carrier for these high melting material.

Product in line 39 is flashed in product flash separator 40 at about 150°F. Overhead, passed to line 41 contains hydrogen, methane, and other light hydrocarbons (principally $C_2$–$C_4$ but including traces of methylcyclopentane). This material may then be passed into a light hydrocarbon absorber unit 45 where 2.58 parts of light hydrocarbons are rejected through 46. Purified hydrogen stream in line 47 containing 7.16 parts hydrogen and 1.53 parts $C_1$–$C_2$ hydrocarbons for a total of 8.69 parts, is divided. 2.69 parts are passed back through lines 33, 12, and 78 to hydroalkylation unit 15 while 6.00 parts are passed back through lines 47, 48, and 37 to dehydrogenating unit 38.

Bottoms from dehydrogenation product flash separator 40 are routed through line 49 to benzene recovery unit 50. Overhead from unit 50 is taken off through line 52 and contains:

| Component | Parts |
|---|---|
| MCP | 0.42 |
| CH | 1.37 |
| B | 110.50 |
| Total | 112.29 |

45.52 parts of this recovered benzene are recycled back through lines 53, 63, and 37 to dehydrogenating operation 38; 66.77 parts of this recovered benzene from line 52 are recycled back through lines 11, 10, 65 and 78 to hydroalkylation unit 15.

Bottoms from benzene recovery unit 50 are taken off through line 51 and routed to $C_7$–$C_8$ aromatic recovery unit 54. 1.51 parts of $C_7$–$C_8$ aromatics are removed overhead through line 55. The 24.61 parts bottoms, containing:

| Component | Parts |
|---|---|
| Biphenyl | 17.40 |

-continued

| Component | Parts |
| --- | --- |
| Terphenyls | 4.53 |
| CHB and related naphthenylbenzenes | 2.32 |
| DCHB and related dinaphthenylbenzenes | 0.36 |
| total | 24.61 | are routed through line 56 to biphenyl-terphenyl recovery unit 60.

Up to 17.40 parts of biphenyl are recovered from line 42 and up to 4.53 parts of terphenyls are recovered from line 43.

The 2.68 parts of reject naphthenylbenzenes (mono and di) are taken off through line 61 and may be drawn off through line 62 as in this embodiment or recycled through lines 63 and 37 to dehydrogenating unit 38.

It is seen then that a total of 29.07 parts of benzene and a net of 0.11 parts of hydrogen are consumed to make the following products:

| Product | Parts |
| --- | --- |
| Biphenyl | 17.40 |
| Terphenyls | 4.53 |
| $C_1-C_2$ gases | 0.48 |
| $C_2-C_4$ | 2.58 |
| $C_7-C_8$ aromatics | 1.51 |
| reject naphthenylaromatics | 2.68 |
| total | 29.18 |

Although this invention has been illustrated by reference to a specific embodiment, it will be apparent to those skilled in the art that various changes and modifications may be made which clearly fall within the scope of this invention.

I claim:

1. The method which comprises hydroalkylating a charge monocyclic aromatic hydrocarbon stream with a hydroalkylating quantity of hydrogen in the presence of hydroalkylation catalyst at hydroalkylation conditions thereby forming a hydroalkylate product stream containing naphthenyl benzenes; dehydrogenating, in the presence of dehydrogenating catalyst at dehydrogenation conditions, a dehydrogenation charge stream containing at least a portion of the naphthenyl benzenes in said hydroalkylate product and at least one diluent-carrier selected from the group consisting of benzene, cyclohexylbenzenes, methylcyclopentane, cyclohexane, toluene, xylene, and mixtures thereof, thereby forming a dehydrogenated product stream containing polyphenyls in diluent-carrier, said diluent-carrier being of lower molecular weight than said product polyphenyls; and recovering said polyphenyls from said dehydrogenated product stream.

2. The method as claimed in claim 1 wherein said charge monocyclic aromatic hydrocarbon is benzene.

3. The method as claimed in claim 1 wherein said diluent-carrier is benzene.

4. The method as claimed in claim 1 wherein said diluent-carrier includes at least one component of the hydroalkylate in addition to naphthenyl benzene.

5. The method as claimed in claim 1 wherein said hydroalkylate product stream is passed directly to the dehydrogenating operation as dehydrogenation charge stream.

6. The method as claimed in claim 1 wherein said hydroalkylate product stream is fractionated to yield (i) a fraction containing increased proportions of mononaphthenyl benzenes and (ii) a fraction containing increased proportions of dinaphthenyl benzenes.

7. The method as claimed in claim 6 wherein said fraction containing increased proportions of mononaphthenyl benzenes is passed to said dehydrogenating operation thereby forming a dehydrogenated product stream containing increased proportions of biphenyl.

8. The method as claimed in claim 6 wherein said fraction containing increased proportions of dinaphthenyl benzenes is passed to said dehydrogenating operation thereby forming a dehydrogenated product stream containing increased proportions of terphenyls.

9. The method which comprises hydroalkylating a charge benzene stream with a hydroalkylating quantity of hydrogen in the presence of hydroalkylation catalyst at hydroalkylation conditions thereby forming a hydroalkylate product stream containing unconverted benzene and naphthenyl benzenes; dehydrogenating, in the presence of dehydrogenating catalyst at dehydrogenation conditions, a dehydrogenation charge stream containing at least the naphthenyl benzenes in said hydroalkylate product and a dehydrogenated product-solubilizing amount of benzene, thereby forming a dehydrogenated product stream containing polyphenyls in benzene; and recovering said polyphenyls from said dehydrogenated product stream.

10. The method which comprises hydroalkylating a charge benzene stream with a hydrogen partial pressure of 50 to 1500 psig in the presence of hydroalkylating catalyst at temperature of 80°–200°C and pressure of 50–1500 psig thereby forming a hydroalkylate product stream containing (i) unconverted benzene and (ii) cyclohexyl benzene; flashing at least a portion of said unconverted benzene from said hydroalkylate product stream in a first flashing operation thereby forming a first flashed hydroalkylate product stream containing a dehydrogenated product-solubilizing amount of benzene; dehydrogenating said first flashed hydroalkylate product stream containing said dehydrogenated product-solubilizing amount of benzene at 700°–1100°F and total pressure of 0–1000 psig thereby forming a fluid dehydrogenated product stream containing polyphenyls in benzene; separating said benzene from said dehydrogenated product stream; and recovering said polyphenyls from said product stream.

11. The method which comprises
dehydrogenating, in the presence of dehydrogenating catalyst at dehydrogenation conditions, a dehydrogenation charge stream containing a naphthenyl benzene and at least one diluent-carrier selected from the group consisting of benzene, cyclohexyl benzene, methyl cyclopentane, cyclohexane, toluene, xylene, and mixtures thereof thereby forming a dehydrogenated product stream containing polyphenyls in diluent-carrier, said diluent-carrier being of lower molecular weight than said polyphenyls; and
recovering said product stream.

12. The method which comprises
dehydrogenating, in the presence of dehydrogenating catalyst at dehydrogenation conditions, a dehydrogenation charge stream containing a cyclohexyl benzene and, as a diluent-carrier, benzene thereby forming a dehydrogenated product stream containing biphenyl and benzene;

separating said benzene from said product stream; and recovering said product stream containing biphenyl.

13. The method which comprises dehydrogenating, in the presence of dehydrogenating catalyst at dehydrogenation conditions, a dehydrogenation charge stream containing a dicyclohexyl benzene and, as a diluent-carrier, benzene or a cyclohexyl benzene thereby forming a dehydrogenated product stream containing terphenyl and diluent-carrier;

separating said diluent-carrier from said product stream; and recovering said product stream containing terphenyl.

\* \* \* \* \*